(12) United States Patent
Tanji et al.

(10) Patent No.: US 6,168,583 B1
(45) Date of Patent: Jan. 2, 2001

(54) BODY WASTE DISPOSABLE ARTICLE HAVING AN OPENING FORMED BY A SURROUNDING WALL

(75) Inventors: Hiroyuki Tanji; Toshifumi Otsubo; Yoshitaka Mishima, all of Kagawa-ken (JP)

(73) Assignee: Uni-Charm Corporation (JP)

( * ) Notice: Under 35 U.S.C. 154(b), the term of this patent shall be extended for 0 days.

(21) Appl. No.: 09/322,532

(22) Filed: May 28, 1999

(30) Foreign Application Priority Data

May 29, 1998 (JP) .................................................. 10-149082
Apr. 23, 1999 (JP) .................................................. 11-117139

(51) Int. Cl.[7] .................................................... A61F 13/15
(52) U.S. Cl. ................... 604/385.14; 604/385.23; 604/385.29; 604/385.19; 604/385.3; 604/385.09; 604/385.01
(58) Field of Search ............................. 604/385.1, 385.01, 604/385.09, 385.3, 385.19, 385.29, 385.23, 385.14

(56) References Cited

U.S. PATENT DOCUMENTS

| | | | |
|---|---|---|---|
| 3,583,402 | * | 6/1971 | Cordell ................................. 128/295 |
| 4,022,212 | * | 5/1977 | Lovison ............................... 128/288 |
| 4,210,143 | * | 7/1980 | De Jonckheere .................... 128/287 |
| 4,246,900 | * | 1/1981 | Schroder ............................. 128/287 |
| 4,662,877 | * | 5/1987 | Williams .............................. 604/385 |
| 4,681,579 | * | 7/1987 | Toussant et al. .................... 604/385 |
| 4,753,645 | * | 6/1988 | Johnson .............................. 604/378 |
| 4,808,178 | * | 2/1989 | Aziz et al. ......................... 604/385.2 |
| 4,834,737 | * | 5/1989 | Khan ................................. 604/385.2 |
| 4,909,803 | * | 3/1990 | Aziz et al. ......................... 604/385.2 |
| 4,964,857 | * | 10/1990 | Osborn ............................... 604/395 |
| 5,005,525 | * | 4/1991 | Stanton ............................... 119/95 |
| 5,069,672 | * | 12/1991 | Wippler et al. ................... 604/385.1 |
| 5,176,672 | * | 1/1993 | Bruemmer et al. ............... 604/385.1 |
| 5,207,665 | * | 5/1993 | Davis et al. ......................... 604/399 |
| 5,217,447 | * | 6/1993 | Gagnon .............................. 604/397 |
| 5,236,428 | * | 8/1993 | Zajaczkowski .................... 604/385.2 |
| 5,241,710 | * | 9/1993 | Lockhart ............................ 2/406 |
| 5,304,160 | * | 4/1994 | Igaue et al. ....................... 604/385.2 |
| 5,325,543 | * | 7/1994 | Allen ................................. 2/406 |
| 5,330,461 | * | 7/1994 | Leeker .............................. 604/385.2 |
| 5,342,342 | * | 8/1994 | Kitaoka ............................. 604/385.2 |
| 5,344,516 | * | 9/1994 | Tanji et al. ........................ 156/164 |
| 5,360,422 | * | 11/1994 | Brownlee et al. ................. 604/385.2 |
| 5,417,680 | * | 5/1995 | Kimura et al. .................... 604/385.2 |
| 5,490,847 | * | 2/1996 | Correa et al. ..................... 604/387 |
| 5,520,674 | * | 5/1996 | Lavon et al. ..................... 604/385.1 |
| 5,567,265 | * | 10/1996 | Zajackowski ...................... 156/256 |
| 5,575,785 | * | 11/1996 | Gryskiewicz et al. ........... 604/385.2 |
| 5,576,091 | * | 11/1996 | Zajackowski et al. ........... 428/192 |
| 5,643,239 | * | 7/1997 | Bodford et al. .................. 604/370 |
| 5,674,213 | * | 10/1997 | Sauer ................................ 604/385.1 |
| 5,814,035 | * | 9/1998 | Gryskiewicz et al. ........... 604/385.1 |
| 5,814,037 | * | 9/1998 | Coates .............................. 604/393 |
| 5,843,067 | * | 12/1998 | Trombetta et al. .............. 604/385.2 |
| 5,895,382 | * | 4/1999 | Popp et al. ....................... 604/385.2 |
| 5,913,851 | * | 6/1999 | Gryskiewicz et al. ........... 604/385.1 |
| 5,935,118 | * | 8/1999 | Gryskiewicz et al. ........... 604/385.1 |
| 5,957,906 | * | 9/1999 | Roe et al. ........................ 604/378 |
| 5,957,907 | * | 9/1999 | Sauer ............................... 604/385.2 |

* cited by examiner

Primary Examiner—John G. Weiss
Assistant Examiner—Paul Shanoski
(74) Attorney, Agent, or Firm—Baker & Daniels

(57) ABSTRACT

A body waste disposable article adapted to receive feces and/or urine discharged thereon, the article having a body fluids absorbent means above which an opening is formed by a surrounding wall partially covering the body fluids absorbent means and surrounding the opening. The article is longitudinally composed of a front end, a rear end and an intermediate region extending between these two ends. The article is configured so as to have the largest width in its intermediate region.

4 Claims, 9 Drawing Sheets

BODY WASTE DISPOSABLE ARTICLE HAVING AN OPENING FORMED BY A SURROUNDING WALL

BACKGROUND OF THE INVENTION

The present invention relates to a method for making a body waste disposable article adapted to be utilized in combination with another article such as a disposable diaper, disposable incontinent pants and the like.

Japanese Patent Application Disclosure Gazette No. 1993-293138 describes a method for forming a body-facing topsheet of a disposable diaper with an elastic opening. This topsheet is provided along a periphery of the opening with an elastic member secured thereto in an extended state so as to describe a circular arc. According to this disclosure, a sheet for forming the topsheet is continuously fed and the elastic member in an extended state is fed while the elastic member is swung transversely of the sheet using traverse means so that the elastic member may describe the circular arcs on the continuous topsheet.

The known method for forming the topsheet of the diaper with the elastic opening is disadvantageous in that, while the sheet can be fed at a relatively high speed, the speed at which the traverse means can be operated is limited and, in consequence, an output per unit time is also restricted. In addition, introduction of the traverse means into the production line for the diaper inevitably leads to an increase of the equipment investment and therefore to a corresponding increase in the manufacturing cost of the diaper.

SUMMARY OF THE INVENTION

In view of the problems as have been described above, it is an object of the present invention to provide a simplified method for making a body waste disposable article such as a disposable diaper having an elastic opening and thereby to solve the problems mentioned above.

According to the present invention, there is provided a body waste disposable article according to a first aspect of the present invention (referred to hereinafter as a first invention), a first method for making this article according to a second aspect of the present invention (referred to hereinafter as the second invention) and a second method for making this article according to a third aspect of the present invention (referred to hereinafter as the third invention.

The first invention relates to a body waste disposable article having a body fluids absorbent means comprising a liquid-previous topsheet, a liquid-impervious backsheet and a liquid-absorbent core disposed therebetween, a surrounding wall being defined by a portion of at least one of the topsheet and the backsheet extending outward beyond a peripheral edge of an absorbent means and folded back to partially cover a top surface of said absorbent means in proximity of the peripheral edge and thereby to leave an opening surrounded by the surrounding wall above a central zone of the absorbent means, and the surrounding wall being elastically stretchable and contractable along an edge of the opening.

In the article as has been described above, the first present invention is characterized in that the absorbent means has a longitudinal direction and a transverse direction being orthogonal to the longitudinal direction in which the absorbent means is composed of a front end, a rear end and an intermediate region extending between these front and rear ends so that the absorbent means is configured to have the largest width in the intermediate region.

The first invention includes various embodiments as follow:

(1) The absorbent means has its width progressively enlarged from the front and rear ends to the intermediate region.

(2) The intermediate region has the largest width at its position a little to the rear end.

(3) The front and rear ends are covered with the surrounding wall.

(4) The opening is provided along its edge with a belt-like elastic member having a width of 5~50 mm and, in the intermediate region, the surrounding wall is bonded to the lower surface of the elastic member along its transversely middle zone so that the elastic member and the surrounding wall present together a substantially T-shaped cross-section when the article is worn by a wearer.

The second invention relates to a method for making a body waste disposable article having a body fluids absorbent means comprising a liquid-previous topsheet, a liquid-impervious backsheet and a liquid-absorbent core disposed therebetween, a surrounding wall being defined by a portion of at least one of the topsheet and the backsheet extending outward beyond a peripheral edge of the absorbent means and folded back to partially cover a top surface of the absorbent means in proximity of the peripheral edge and thereby to leave an opening surrounded by the surrounding wall above a central zone of the absorbent means, and the surrounding wall being elastically stretchable and contractable along an edge of the opening.

In the method as has been described above, the second invention is characterized by that the method comprises the steps of:

a. covering the core with the topsheet and the backsheet which are, in turn, bonded to each other along portions of the topsheet and the backsheet extending outward beyond a peripheral edge of the core to obtain a laminate;

b. bonding elastic members to any one of the topsheet and the backsheet with a rectilinear tension along transversely opposite edges of the topsheet or the backsheet extending in parallel to each other with the core lying therebetween;

c. folding the laminate back onto itself with the topsheet lying inside so that the elastic members on the side edges may be placed upon each other;

d. bonding respective halves of the laminate, which has been folded back onto itself, to each other along a pair of imaginary lines intersecting the side edges and extending in parallel to each other with the core lying therebetween; and e. releasing the elastic members to contract after the step d.

According to an embodiment of the second invention, the elastic members are belt-like elastic members each being 5~50 mm wide and secured to the side edges along a transversely middle line of this belt-like elastic member. The method according to the second invention may further comprise a step of forming the backsheet with means used to fasten the article to a wearer's garment.

The third invention also relates to a method for making a body waste disposable article having a body fluids absorbent means comprising a liquid-previous topsheet, a liquid-impervious backsheet and a liquid-absorbent core disposed therebetween, a surrounding wall being defined by a portion of at least one of the topsheet and the backsheet extending outward beyond a peripheral edge of the absorbent means and folded back to partially cover a top surface of the absorbent means in proximity of the peripheral edge and thereby to leave an opening surrounded by the surrounding wall above a central zone of the absorbent means, and the surrounding wall being elastically stretchable and contractable along an edge of the opening.

In the method as has been described above, the third invention is characterized by that the method comprises the steps of:

a. continuously feeding a first web for forming the topsheet and a second web for forming the backsheet in one direction, respectively;
b. continuously feeding the elastic members in the one direction and securing them with a rectilinear tension to any one of the first and second webs along transversely opposite side edges of the web;
c. intermittently feeding the cores in the one direction onto any one of the first and second webs in transversely middle regions of the web;
d. placing the first and second webs upon each other to sandwich the cores therebetween, after the elastic members and the cores have been fed, and thereby to form a third web comprising these first and second webs, elastic members and cores;
e. folding the third web back onto itself with the first web lying inside so that the elastic members on the side edges may be placed upon each other;
f. bonding mutually facing halves of the first web making the part of the third web, which has been folded back onto itself, to each other in a region of the third web extending between each pair of the adjacent cores;
g. cutting the third web which has been folded onto and bonded to itself on the step f in the region extending between each pair of the adjacent cores along an imaginary line extending transversely of the third web so that the region may partially remain on both sides of the imaginary line; and
h. releasing the elastic members to contract after the step g.

According to an embodiment of the third invention, the elastic members are belt-like elastic members each being 5~50 mm wide and bonded to the side edges along a transversely middle line of the belt-like elastic member. The method according to the third invention may further comprise a step of forming the second web with means used to fasten the article to a wearer's garment.

DETAILED DESCRIPTION OF THE PREFERRED EMBODIMENTS

Details of a method for making a body waste disposable article according to the present invention will be more fully understood from the description given hereunder with reference to the accompanying drawings.

Figure 1:
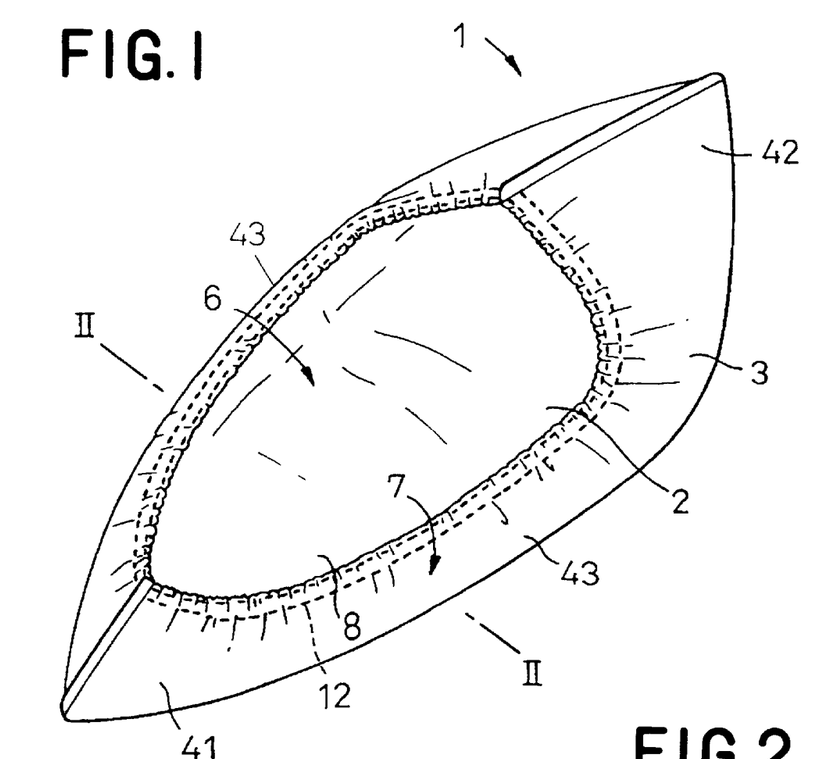
FIG. 1 is a perspective view of an embodiment of a body waste disposable article according to the present invention.
Figure 2:
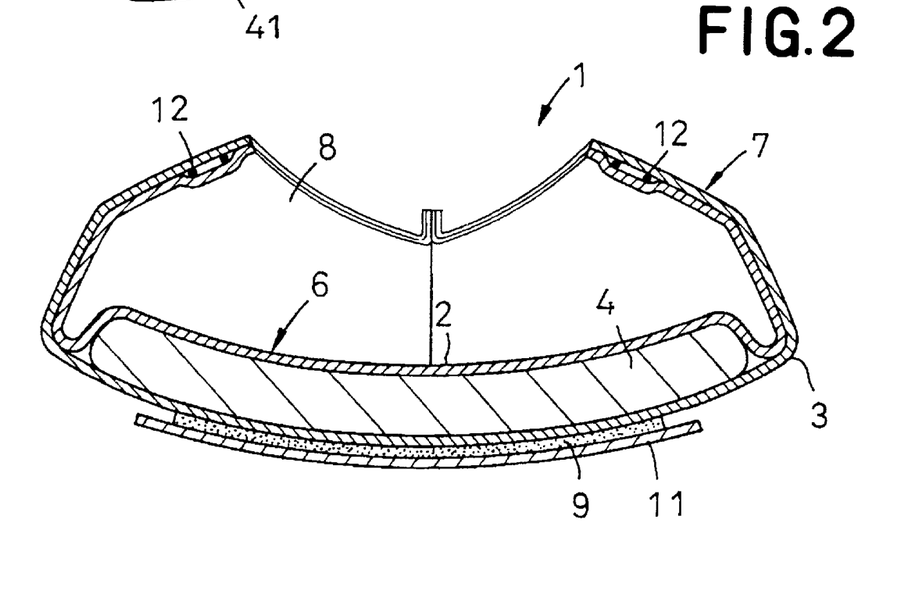
FIG. 2 is a sectional view taken along a line II—II in FIG. 1.

FIG. 1 is a perspective view showing a body waste disposable article 1 and FIG. 2 is a sectional view taken along a line II—II in FIG. 1. The article 1 is adapted to receive body wastes, particularly feces discharged thereon and suitable for utilization in combination with a diaper, a diaper cover or an undergarment worn by a wearer.

The disposable article 1 comprises a liquid-previous topsheet 2, a liquid-impervious backsheet 3 and an absorbent core 4 disposed between these two sheets 2, 3. The topsheet 2 and the backsheet 3 and the core 4 form a body fluids absorbent means 6. Portions of the topsheet 2 and the backsheet 3 extending outward beyond a peripheral edge of the core 4 are folded back upward along the peripheral edge of the core 4, after they have been placed upon and bonded to each other, to form a surrounding wall 7. Above the top surface of the body waste absorbent means 6 in proximity of its central zone, there is formed an opening 8 surrounded by the surrounding wall 7. The surrounding wall 7 has an elastic member 12 extending in a ring-shape along a periphery of the opening 8 and secured in an extended state to an inner surface of at least one of the topsheet 2 and the backsheet 3. The disposable article 1 is longitudinally composed of a tapering front end 41, a tapering rear end 42 and an intermediate region 43 extending between these two ends 41, 42. The disposable article 1 has its width progressively enlarged from the front and rear ends 41, 42 toward the intermediate region 43 and is configured to have its largest width at a position a little to the rear end 42. The backsheet 3 constituting the absorbent means 6 is applied on its lower surface with an adhesive agent 9 and protectively covered with a release sheet 11.

Figure 3:
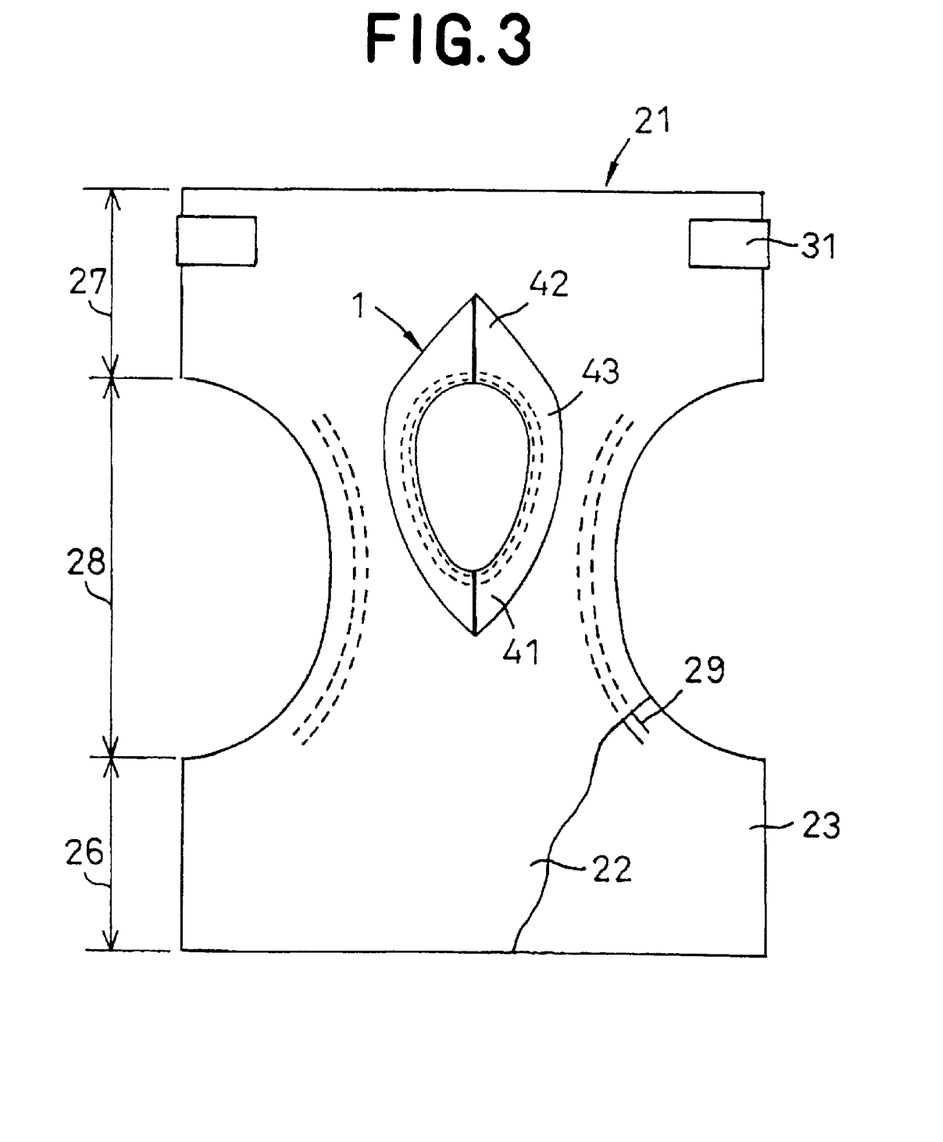
FIG. 3 is a plan view showing the disposable article as attached to a diaper cover.

FIG. 3 is a plan view showing the disposable article 1 as attached to a diaper cover 21 having partially cut away. The diaper cover 21 comprises a laminate of a topsheet 22 made of a plastic film and a backsheet 23 made of a nonwoven fabric and has a hourglass-shape. The diaper cover 21 is longitudinally composed of a front waist region 26, a rear waist region 27 and a crotch region 28 extending between these two waist regions 26, 27. Transversely opposite side edges of the crotch region 28 are curved inwardly of the diaper cover 21. The crotch region 28 is provided along its side edges with elastic members 29 adapted to surround a wearer's legs and these elastic members 29 are secured in an extended state to an inner surface of at least one of the topsheet 22 and the backsheet 23. The disposable article 1 having the release sheet 11 peeled off is detachably fastened by means of the adhesive agent 9 to an inner surface of the diaper cover 21 over its zone extending across the rear waist region 27 and the crotch region 28. It is possible for the disposable article 1 to be attached to the diaper cover 21 over its zone selected depending on a wearer's body characteristics.

The diaper cover 21 is provided on transversely opposite side edges of the rear waist region 27 with tape fasteners 31 by means of which an assembly of the disposable article 1 and the diaper cover 21 as shown in FIG. 3 and can be worn substantially in the same manner as the conventional disposable diaper is worn so that the wearer's anus may lie substantially in a central zone of the opening 8 of the disposable article 1.

With the disposable article 1 utilized in the manner as has been described above, feces is properly discharged into the opening 8 and the diaper cover 21 is well prevented from being soiled with feces. For disposable of the feces, it is unnecessary to handle the diaper cover 21 of a relatively large size and only the article 1 of a relatively small size may be handled. Accordingly, operation of the disposable is correspondingly alleviated. By placing the tapering front end 41 in the crotch region 28 when the diaper cover 21 is worn, the front end 41 is smoothly received between the wearer's legs and the disposable article 1 is not uncomfortable for the wearer. The disposable article 1 is adequately wide in proximity of the rear end 42 and can receive a large amount of feces. It is also possible to increase an adhesive strength of the adhesive agent so that the disposable article 1 may be permanently attached to the diaper cover 21. The disposable article 1 can be attached also to an inner surface of the disposable diaper or undergarments, instead of being attached to the diaper cover 21.

Figures 4A, 4B:
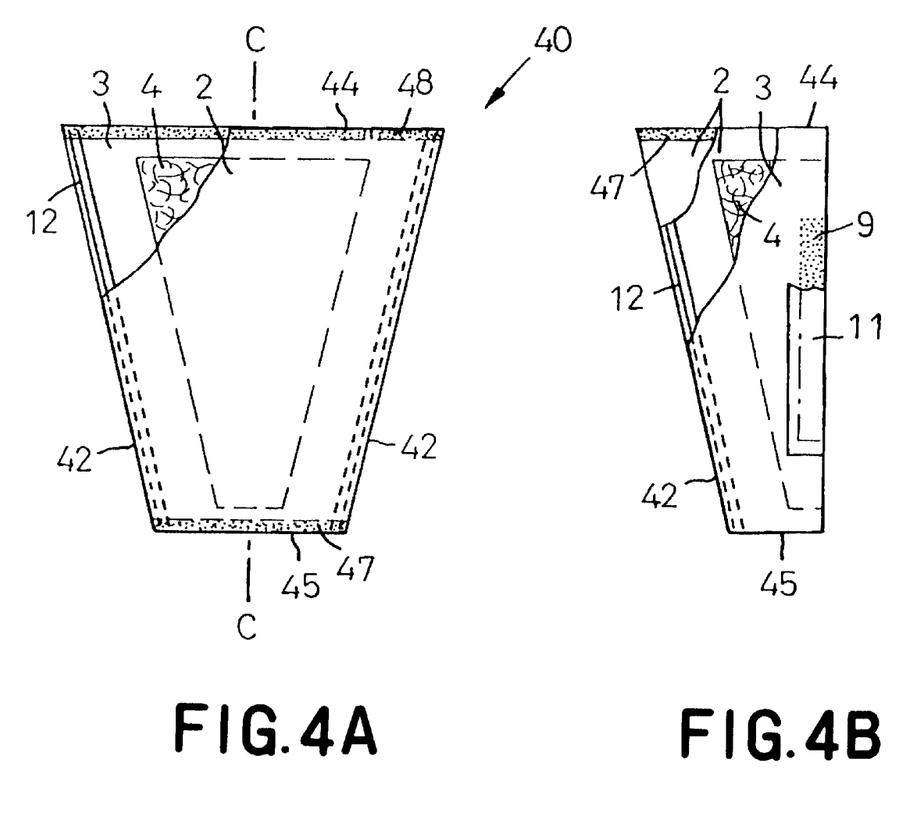
FIGS. 4A–4C are a diagram exemplarily illustrating the steps for making the disposable article.
Figure 4C:
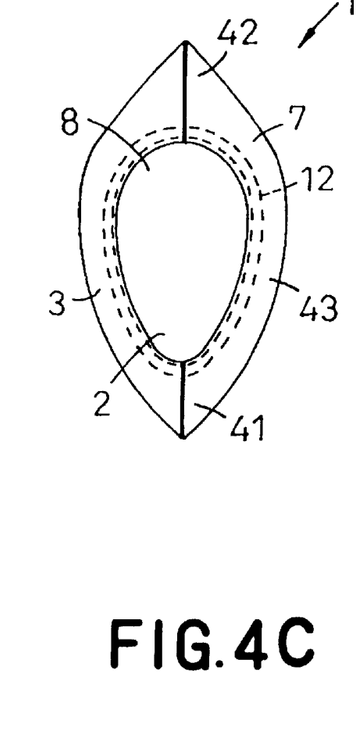

FIGS. 4A–4C are diagrams illustrating the steps 4A–4C for making the disposable article 1 shown in FIG. 1. In the step 4A, the liquid-previous topsheet 2 and the liquid-impervious backsheet 4C both having an inverted trapezoidal shape of an identical size are placed upon each other with the absorbent core 4 disposed therebetween in a central zone of these two sheets 2, 3; then, the portions of these two sheets 2, 3 extending outward beyond the peripheral edge of the core 4 are bonded together by means of hot melt adhesive (not shown) to form a trapezoidal laminate 40. The laminate 40 has transversely opposite side edges 42, 42, longitudinally opposite end edges 44, 45 both extending between the side edges 42, 42, wherein the end edge 44 is dimensioned to be longer than the end edge 45. Inside the side edges 42, 42 of the laminate 40, the elastic members 12, 12 are secured with a rectilinear tension to the laminate 40 by means of hot melt adhesive (not shown). In this embodiment illustrated, these elastic members 12, 12 are disposed between the topsheet 2 and the backsheet 3 and bonded to the inner surface of at least one of the topsheet 2 and the backsheet 3. The core 4 may be bonded to at least one of the topsheet 2 and the backsheet 3. As will be apparent from FIG. 4B, the adhesive agent 9 previously applied on the backsheet 3 is protectively covered with the release sheet 11.

In the step 4B, the laminate 40 is folded along a center line C—C back onto itself with the topsheet 2 lying inside and bonded together along the end edges 44, 45, both placed upon themselves as the laminate 40 is folded back, respectively, by means of hot melt adhesive agents 47, 48 (See the step 4B). The adhesive agent 9 having been applied on the backsheet 3 prior to the step b is protectively covered with the release sheet 11. It should be understood that the laminate 40 folded back is shown in FIG. 4B as partially cut away.

In the step 4C, the elastic members 12, 12 are released to contract. Such contraction of the elastic members 12, 12 causes the portion of the topsheet 2 and the backsheet 3 extending outward beyond the peripheral edge of the core 4 to be bent inward along the peripheral edge of the core 4 with the topsheet 2 lying inside. The portions of the topsheet 2 and the backsheet 3 bent inward define the surrounding wall 7 which partially covers the core 4 in proximity of its peripheral edge and leaves the opening 8 above the central zone of the core 4. Of the laminate 40, a region in proximity of the end edge 44 forms the front end 41 and a region in proximity of the end edge 45 forms the rear end 42. In this way, the disposable article 1 shown in FIGS. 1 and 2 is obtained, in which the respective elastic members 12, 12 describe circular arcs along the periphery of the opening 8.

The region extending between the front and rear ends 41, 42 is curved outwardly of the disposable article 1 and a depth of the disposable article 1 from the opening 8 to the core 4 increases as a degree of contraction exhibited by each of the elastic members 12, 12.

Figure 5:
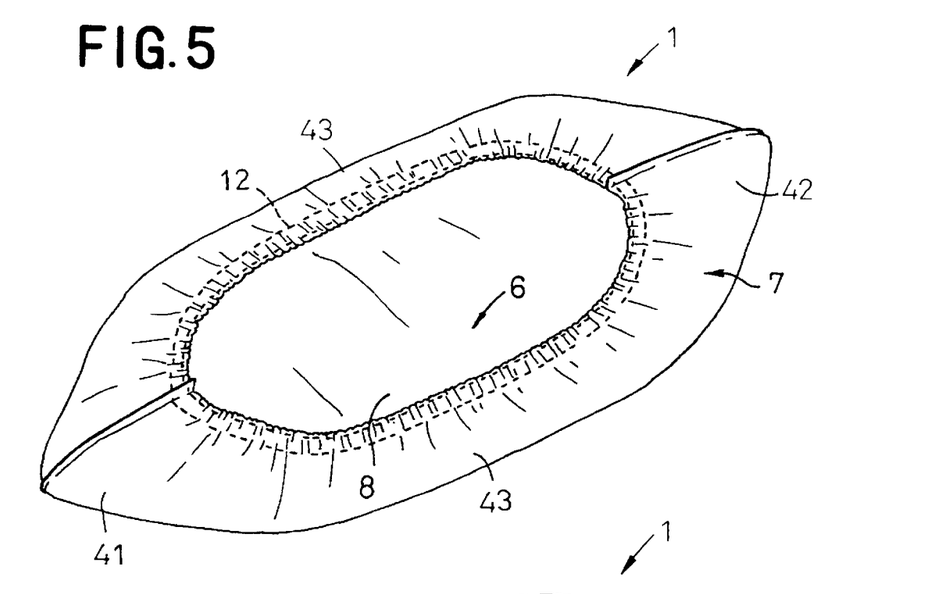
FIG. 5 is a view similar to FIG. 1 showing another embodiment of the disposable article according to the present invention.

FIG. 5 is a view similar to FIG. 1 showing an alternative embodiment of the disposable article 1. In this disposable article 1, a degree at which the front end 41 is tapered is substantially the same as a degree at which the rear end 42 is tapered. Between these front and rear ends 41, 42, the intermediate region 43 has a substantially uniform width. As far as the cross-sectional shape is concerned, no difference is found between these two embodiments.

Figure 6:
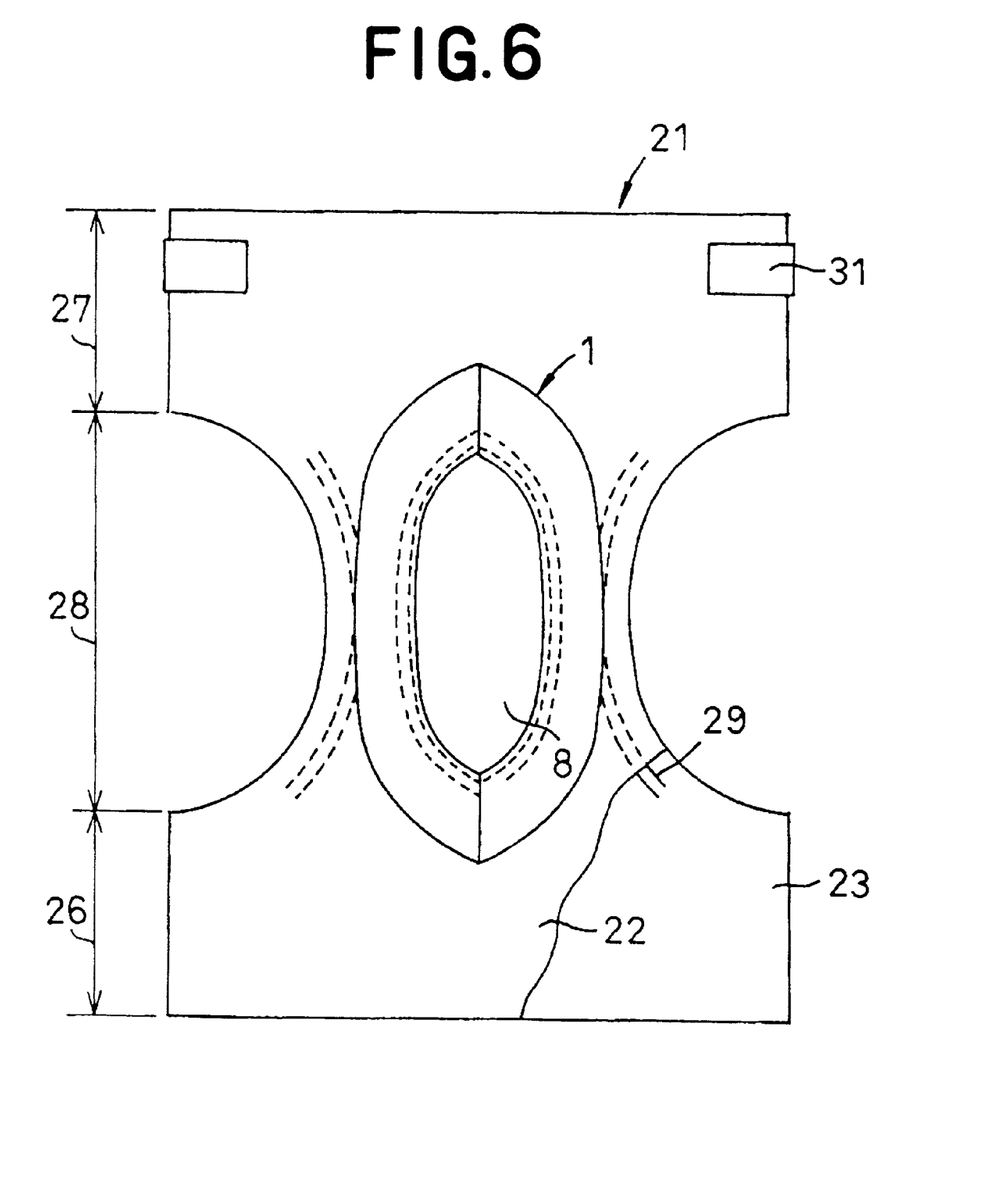
FIG. 6 is a plan view showing the disposable article of FIG. 5 as attached to the diaper cover.

FIG. 6 is a plan view showing the disposable article 1 of FIG. 5 as attached to the crotch region 28 of the diaper cover 21. The disposable article 1 shown in FIG. 6 is characterized by that a dimension between the front and rear ends 41, 42 is longer than in the embodiment shown in FIG. 3 and the opening 8 is correspondingly larger. Such an arrangement allows feces and urine to be more reliably received by the larger opening 8.

Figure 7:
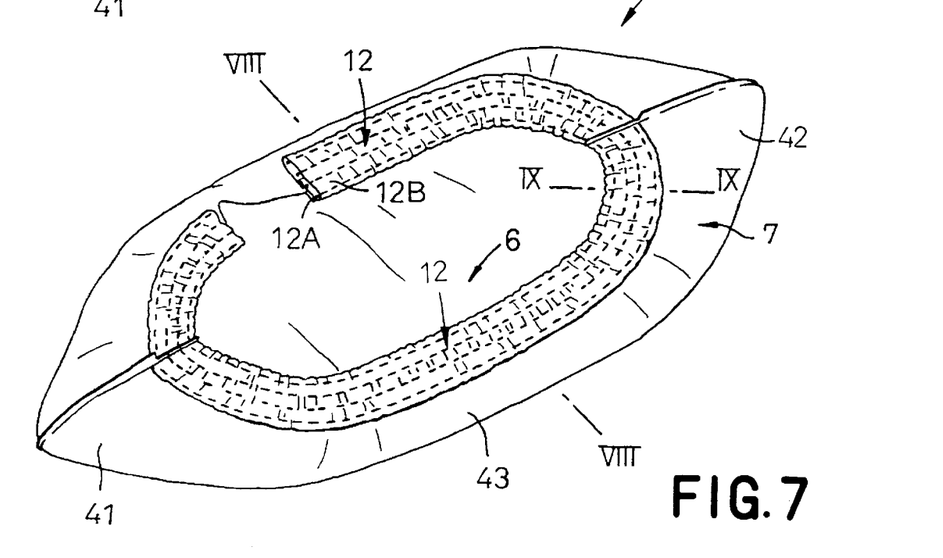
FIG. 7 is a perspective view showing still another embodiment of the disposable article having partially cut away.
Figure 8:
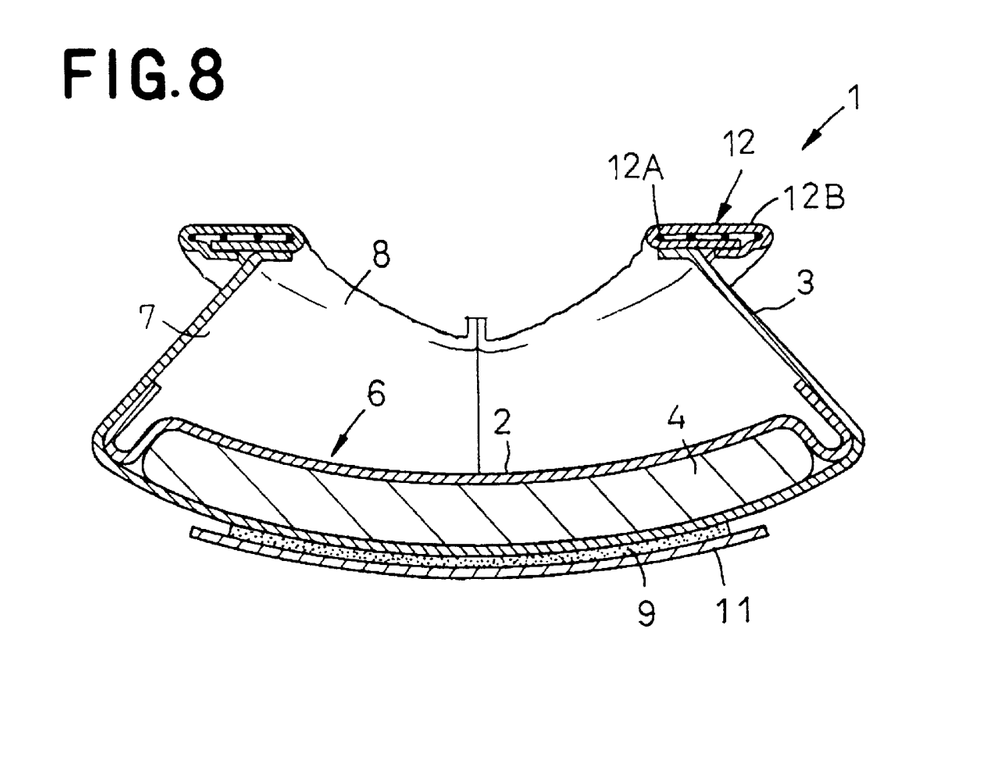
FIG. 8 is a sectional view taken along a line VIII—VIII in FIG. 7.
Figure 9:
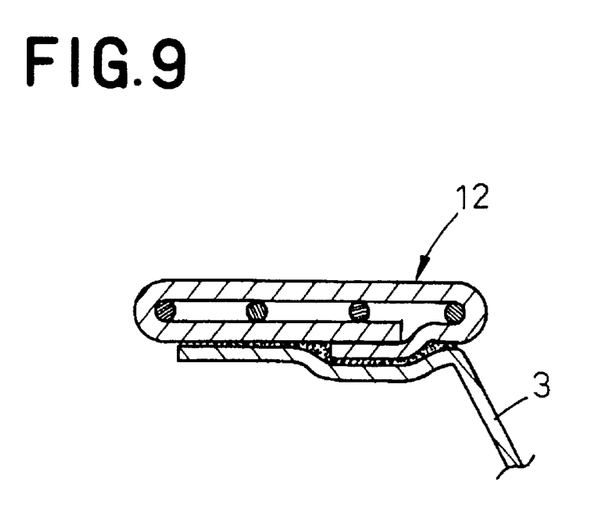
FIG. 9 is a sectional view taken along a line IX—IX in FIG. 7.

FIG. 7 is a view similar to FIG. 5 showing still another embodiment of the disposable article 1 having partially cut away and FIGS. 8, 9 are sectional views taken along lines VIII—VIII and IX—IX in FIG. 7. According to this embodiment of the disposable article 1, the opening 8 is provided along its periphery with the belt-like elastic members 12, 12 being 5~50 mm wide and forming together a loop. Each of the elastic members 12, 12 comprises a plurality of rubber threads 12A put under appropriate tension and covered with a nonwoven fabric 12B. The portion of the backsheet 3 folded back inwardly of the article 1 is bonded to the elastic member 12 along its transversely middle zone. With the article 1 being put on a wearer's body, the elastic members 12, 12 cooperate with the backsheet 3 in the intermediate region 43 extending between the front and rear ends 41, 42 to lift off above the absorbent means, presenting a substantially T-shaped cross-section (See FIG. 8). At the same time the elastic members 12, 12 are spaced from each other to describe an enlarged loop which is placed against a wearer's skin and reliably prevents feces and urine from leaking out beyond the peripheral edge of the article 1. In order to ensure that the elastic members 12, 12 cooperate with the backsheet 3 to present the cross-section as shown in FIG. 8, it is preferred to arrange a plurality of rubber threads 12A describing a loop so that the stretch stress should gradually increase from the outermost rubber thread to the innermost rubber thread of the respective elastic members 12. In proximity of the front and rear ends of the article 1, the elastic members 12, 12 are preferably secured substantially over their entire width to an outer surface of the backsheet 3 as shown in FIG. 9. The article 1 shown in FIG. 8 is distinguished from the article 1 shown in FIG. 2 in that the portion of the backsheet 3 extending outward beyond the peripheral edge of the core 4 and folded back is longer than the corresponding portion of the topsheet 2. The surrounding wall 7 partially covering the body fluids absorbent means 6 along its peripheral edge is substantially defined by the backsheet 3.

Figure 10:
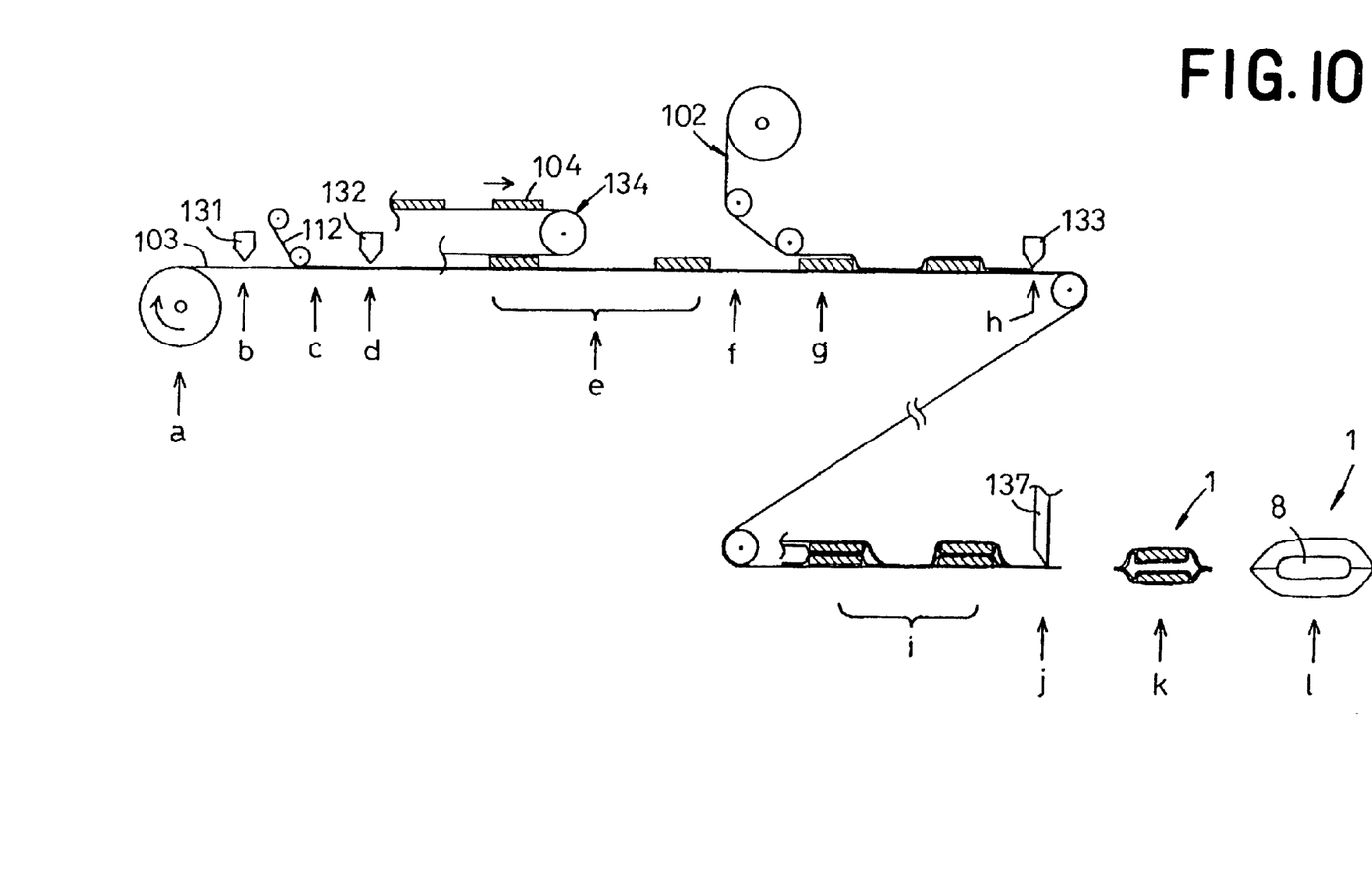
FIG. 10 is a side view schematically illustrating the steps for making the disposable article of FIG. 5.
Figure 11:
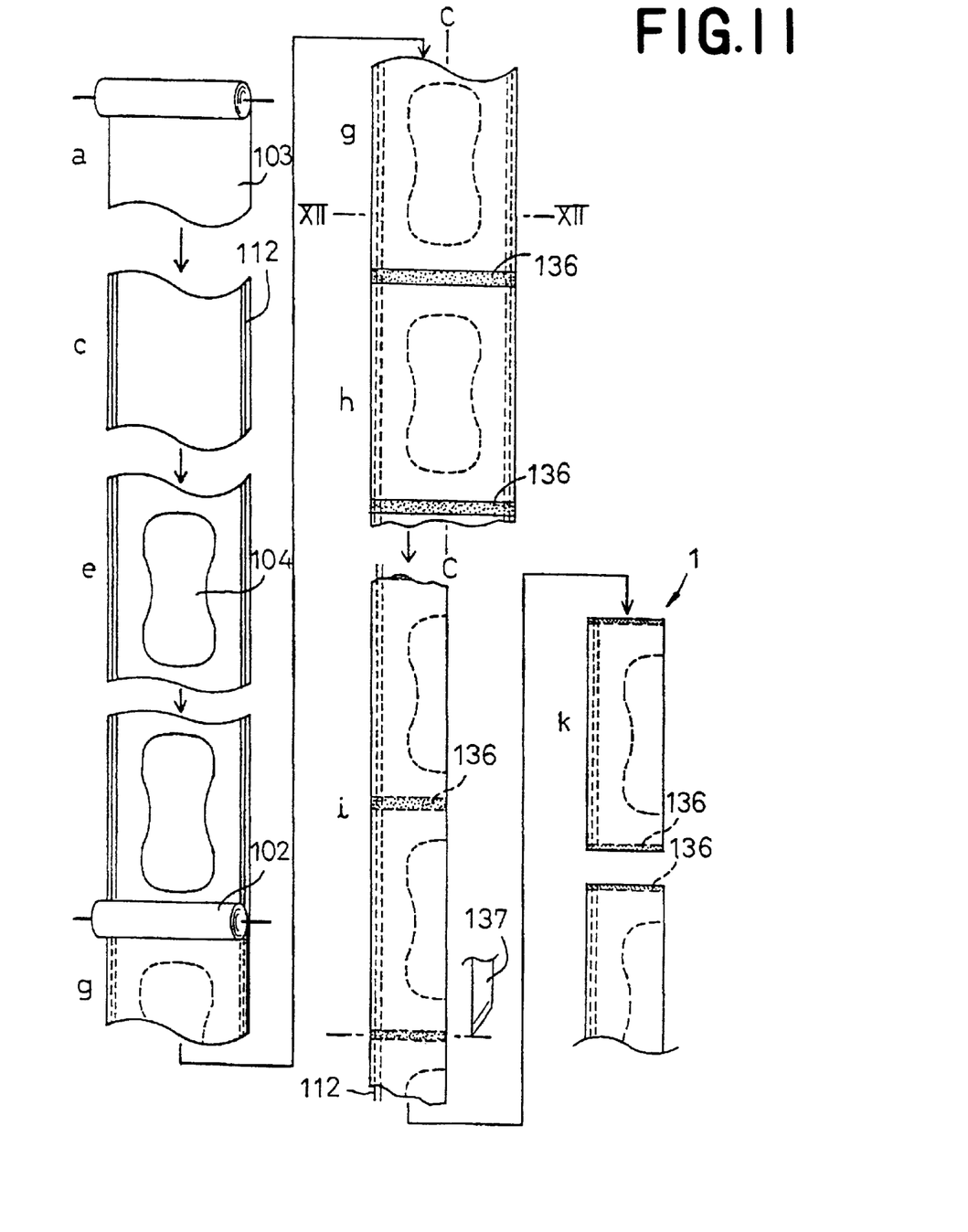
FIG. 11 is a plan view showing an important part of the steps schematically illustrated by FIG. 10.

FIG. 10 is a side view schematically illustrating the steps for continuously making the disposable article 1 shown in FIG. 5 and FIG. 11 is a plan view showing an important part in the side view. FIG. 10 illustrates the steps g~k with a nonwoven fabric 102 and a plastic film 103 really covering a core 104 cut away in order that the absorbent core 104 can be seen.

Referring to FIGS. 10 and 11, on the step a, a web of liquid-impervious plastic film 103 for forming the backsheet 3 of the body fluids absorbent means 6 is continuously fed from the left to the right as viewed in FIG. 10 (from the top to the bottom as viewed in FIG. 11).

On the step b, hot melt adhesive (not shown) is discharged from a first nozzle 131 and applied on the film 103 along its transversely opposite side edges.

On the step c, elastic members 112 with a rectilinear tension are continuously fed and secured to the film 103 immediately inside its transversely opposite side edges by means of the hot melt adhesive which has been applied thereon on the previous step b.

On the step d, hot melt adhesive (not shown) is discharged from a second nozzle 132 and intermittently or continuously applied on the film 103 transversely as well as longitudinally thereof.

On the step e, the absorbent cores 104 transported by a feeder 134 are intermittently placed on the film 103 in its transversely middle zone in a longitudinal direction of the film 103 and bonded to the film 103 by means of the hot melt adhesive which has been applied thereon on the previous step d.

On the steps of f and g, the web of the liquid-previous nonwoven fabric 102 for forming the topsheet 2 of the body fluids absorbed nl means 6 is continuously fed. The nonwoven fabric 102 having a width substantially the same as the width of the film 103 covers the film 103 over its full width together with the cores 104 and is bonded to the film 103 by means of the hot melt adhesive which has been applied thereon on the previous step d. In this manner, the web comprising the nonwoven fabric 102, the film 103 and the cores 104 is obtained.

On the step h, adhesive 136 discharged from a third nozzle 133 (See FIG. 11) is applied on an upper surface of the nonwoven fabric 102 so that the adhesive(136)-applied zone extends transversely across the nonwoven fabric 102 between each pair of the adjacent cores 104. The adhesive 136 should be applied on the nonwoven fabric 102 at least over a half of its full width, i.e., over an extent defined from one of its side edges to the center line C—C (See FIG. 11). In the case illustrated, the adhesive 136 is applied on the nonwoven fabric 102 over its full width.

On the step i, the nonwoven fabric 102 and the film 103 placed upon each other are folded back along the center line C—C with the nonwoven fabric 102 lying inside and respective halves of the nonwoven fabric 102 are bonded together by means of the adhesive 136.

On the steps j and k, the nonwoven fabric 102 and the film 103 placed upon each other is cut by a cutter 137 so that each of the adhesive(136)-applied zones may be divided in two as viewed in the machine direction to obtain the individually folded disposable articles 1.

On the step 1, the disposable article 1 obtained on the previous steps j and k is unfolded. As the article 1 is unfolded, the elastic members 112 are released to contract. Upon contracting of the elastic members 112, the respective portions of the nonwoven fabric 102 and the film 103 extending outward beyond the peripheral edge of the core 104, placed upon and bonded to each other are curved inward along the peripheral edge of the core 104. The respective portions form the surrounding wall 7 as shown in FIG. 5, which forms, in turn, the opening 8. However, there may be a case in which the disposable article 1 is supplied to consumers without being unfolded as shown in FIG. 5 and unfolded by the consumers immediately before the article 1 is actually utilized. In this case, the step 1 can be eliminated.

The nonwoven fabric 102, the film 103, the core 104 and the elastic members 112 which have been used on the steps for making the disposable article 1 are respectively destined to form the topsheet 2, the backsheet 3, the core 4 and the elastic members 12 of each finished disposable article 1.

Figure 12:
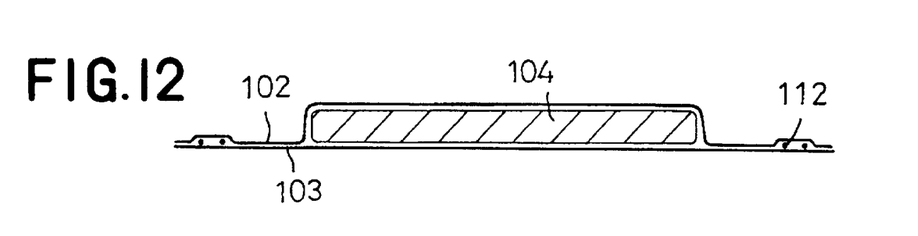
FIG. 12 is a sectional view taken along a line XII—XII in FIG. 11.

FIG. 12 is a sectional view of the web obtained on the step g as taken along a line XII—XII in FIG. 11. As will be apparent from FIG. 12, the core 104 and the elastic members 112 are covered with the nonwoven fabric 102 and the film 103.

Figure 13:
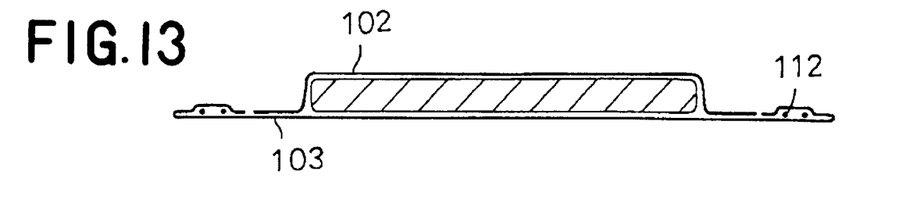
FIG. 13 is a view similar to FIG. 12 showing a specific embodiment of a web.

FIG. 13 is a view similar to FIG. 12, showing another embodiment of the web obtained on the step g illustrated in FIG. 11. According to this embodiment, the side edges of the film 103 are folded back to cover the elastic members 112, respectively. To obtain the disposable article 1 according to this embodiment, the film 103 having a width larger than that of the nonwoven fabric 102 may be used and the steps illustrated in FIG. 10 may be added with a step of folding the side edges of the film 103 as shown.

Figure 14:
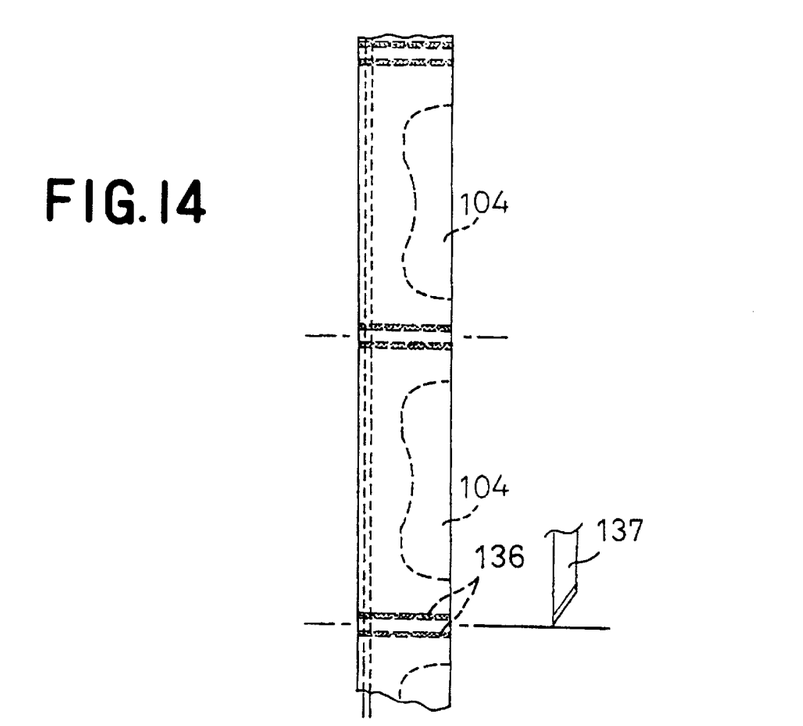
FIG. 14 is a fragmentary diagram exemplarily showing a part of the steps for making the disposable article.

FIG. 14 is a view corresponding to the step i in FIG. 11, showing an alternative embodiment of the present invention. In the case of this embodiment, a pair of the adhesive(136)-applied zones extend in parallel to each other between a pair of the adjacent cores 104. On the subsequent step j, the web is cut between the pair of the adjacent adhesive(136)-applied zones. The disposable article 1 obtained in this manner is advantageously free from an apprehension that the adhesive 136 might be exposed along end surfaces given by the step j of cutting and offensively stimulate a wearer's skin.

For exploitation of the present invention, it is also possible to bond the respective members of the disposable article 1 by using the well known heat-sealing technique instead of using the adhesive agent so far as the members to be bonded to each other are of heat-sealable materials. While the adhesive 9 shown in FIG. 2 is not essential for the disposable article 1, a step of applying the adhesive 9 may be inserted into the course from the step b to the step h illustrated in FIG. 10, if necessary. It is also possible to replace the adhesive 9 by a hook or loop member making a part of the mechanical fastener which is well known under the trademark "VELCRO" or "MAGIC TAPE". Specifically, the hook or loop member bonded to the backsheet 3 may be used to fasten the disposable article 1 to an undergarment such as a diaper cover.

The body waste disposable article according to the present invention enables it to receive and hold feces exclusively and thereby to prevent the diaper as a whole from being soiled with feces. The article is tapered toward its front end so that the article may be smoothly placed against a wearer's crotch zone.

The method according to the present invention for making the body waste disposable article enables it to rectilinearly feed the elastic members by eliminating use of the traverse means as has been essential for the prior art to swing the elastic members in the course of attaching the elastic members along the periphery of the opening. As a consequence, there is no apprehension that a productivity for the disposable article might be adversely affected by a feeding rate of the elastic members which would be inevitably restricted by use of the traverse means. In addition, such rectilinear manner of feeding the elastic members enables the feeding equipment to be correspondingly simplified and thereby undesirable increase in the cost of the disposable article due to the equipment investment can be avoided.

What is claimed is:

1. A body fluids absorbent article for use in conjunction with a means for supporting the same against the body of a wearer, which body fluids absorbent article comprises:

a liquid-pervious topsheet:

a liquid-impervious backsheet;

a liquid-absorbent core disposed between the liquid-pervious topsheet and the liquid-impervious backsheet;

a surrounding wall defined by a portion of at least one of said liquid-pervious topsheet and said liquid-impervious backsheet, said surrounding wall extending outward beyond a peripheral edge of said liquid absorbent core and folded back to partially cover a peripheral portion of a top surface of said liquid-absorbent core and thereby provide an opening surrounded by said surrounding wall, whereby said opening is above a central zone of said liquid-absorbent core, said surrounding wall being elastically stretchable and contractible along an edge of said opening; and an adhesive layer on a bottom surface of the liquid-impervious backsheet for removably coupling the body fluids absorbent article to a means for supporting the same against the body of a wearer, said absorbent means having a longitudinal direction and a transverse direction which is orthogonal to said longitudinal direction, said absorbent means being composed along said longitudinal direction of a front end, a rear end and an intermediate region extending between the front and rear end so that said absorbent means is configured to have a largest width in said intermediate region.

2. The article according to claim 1, wherein said absorbent means has a width which progressively increases from said front and rear ends toward said intermediate region.

3. The article according to claim 1, wherein said the largest width of the intermediate region is offset from a center of the absorbent means toward said rear end.

4. The article according to claim 1, wherein said front and rear ends are covered by said surrounding wall.

* * * * *